United States Patent
Simeone et al.

(10) Patent No.: US 11,850,389 B2
(45) Date of Patent: Dec. 26, 2023

(54) INK SUPPLY UNIT FOR A TATTOOING DEVICE

(71) Applicant: Plus System S.R.L.S., Pordenone (IT)

(72) Inventors: Giulio Simeone, Padua (IT); Antonio Trani, Dueville (IT)

(73) Assignee: Plus System S.R.L.S., Pordenone (IT)

( * ) Notice: Subject to any disclaimer, the term of this patent is extended or adjusted under 35 U.S.C. 154(b) by 525 days.

(21) Appl. No.: 17/266,276

(22) PCT Filed: Sep. 26, 2019

(86) PCT No.: PCT/IB2019/058161
§ 371 (c)(1),
(2) Date: Feb. 5, 2021

(87) PCT Pub. No.: WO2020/065567
PCT Pub. Date: Apr. 2, 2020

(65) Prior Publication Data
US 2021/0299423 A1    Sep. 30, 2021

(30) Foreign Application Priority Data
Sep. 28, 2018 (IT) .......... 102018000008997

(51) Int. Cl.
*A61M 37/00*     (2006.01)
(52) U.S. Cl.
CPC ... *A61M 37/0084* (2013.01); *A61M 2205/071* (2013.01); *A61M 2205/123* (2013.01)
(58) Field of Classification Search
CPC .............. A61M 37/00; A61M 37/0015; A61M 37/0076; A61M 37/0084;
(Continued)

(56) References Cited

U.S. PATENT DOCUMENTS 4,798,582 A * 1/1989 Sarath .................... B43K 1/003
604/47

FOREIGN PATENT DOCUMENTS

ES   1 069 167 U   2/2009
GB   1 331 024 A   9/1973
(Continued)

OTHER PUBLICATIONS

International Search Report and Written Opinion dated Jan. 24, 2020, issued in PCT Application No. PCT/IB2019/058161, filed Sep. 26, 2019.

*Primary Examiner* — Robert J Scruggs
(74) *Attorney, Agent, or Firm* — Workman Nydegger

(57) ABSTRACT

A unit for supplying ink to the needles of a tattooing device includes a handling unit, in which the following can be found: a grip; a removable tip provided at one end with one or more tattooing needles; a coupling element configured to connect the grip and the tip to each other; a driver operatively associated with the grip to move the needles by imparting a reciprocating rectilinear motion to them; one or more tanks for containing the ink, operatively associated with the handling unit. The ink supply unit includes an air movement unit driven by the driver and mechanically connected to the handling unit. The air movement unit is configured to push the air moved by the driver toward the tank, the tank for containing the ink communicating with the air movement unit by a valve. Once conveyed into the tank by the valve, the air forces the ink to be dispensed from the tank onto the needles.

11 Claims, 9 Drawing Sheets

(58) Field of Classification Search
CPC ...... A61M 2205/071; A61M 2205/123; A61M 2207/00; A61B 5/0532; A61B 5/46; A61B 17/3401; A61B 17/3403; B26F 1/32; A01K 11/005; Y10T 74/18056
See application file for complete search history.

(56) References Cited

FOREIGN PATENT DOCUMENTS

| | | |
|---|---|---|
| KR | 101 831 124 B1 | 4/2018 |
| WO | 2015/127909 A1 | 9/2015 |

\* cited by examiner

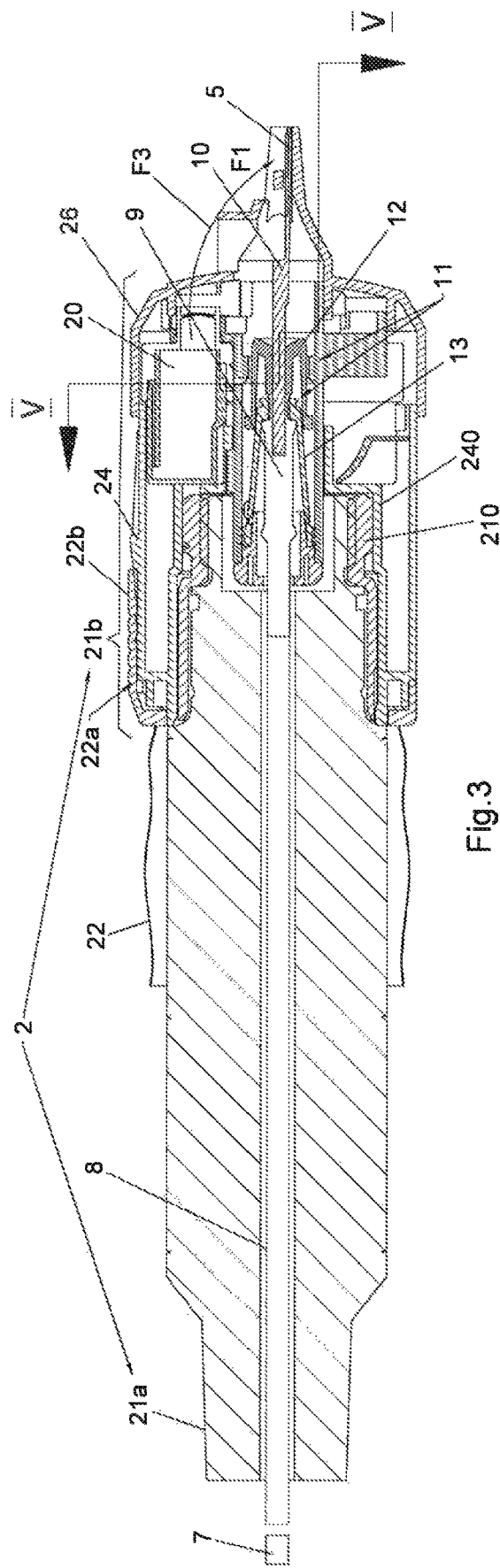
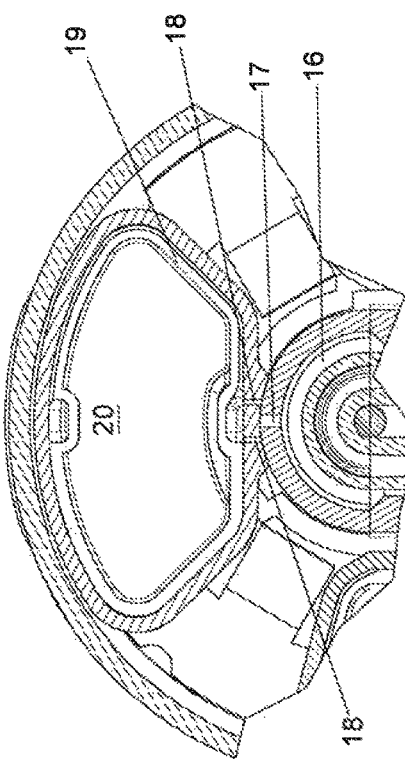
Fig.3
Fig.5

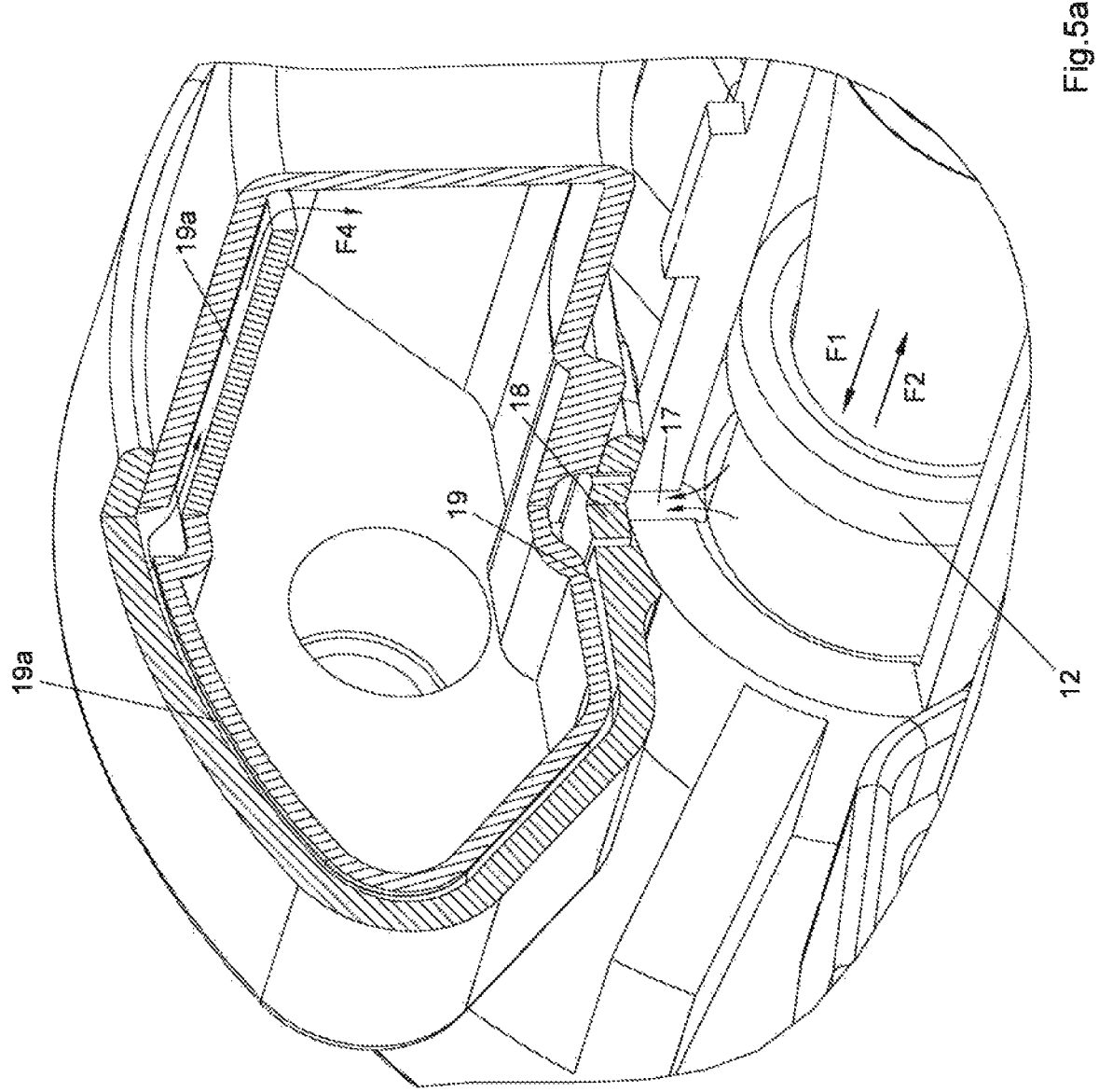

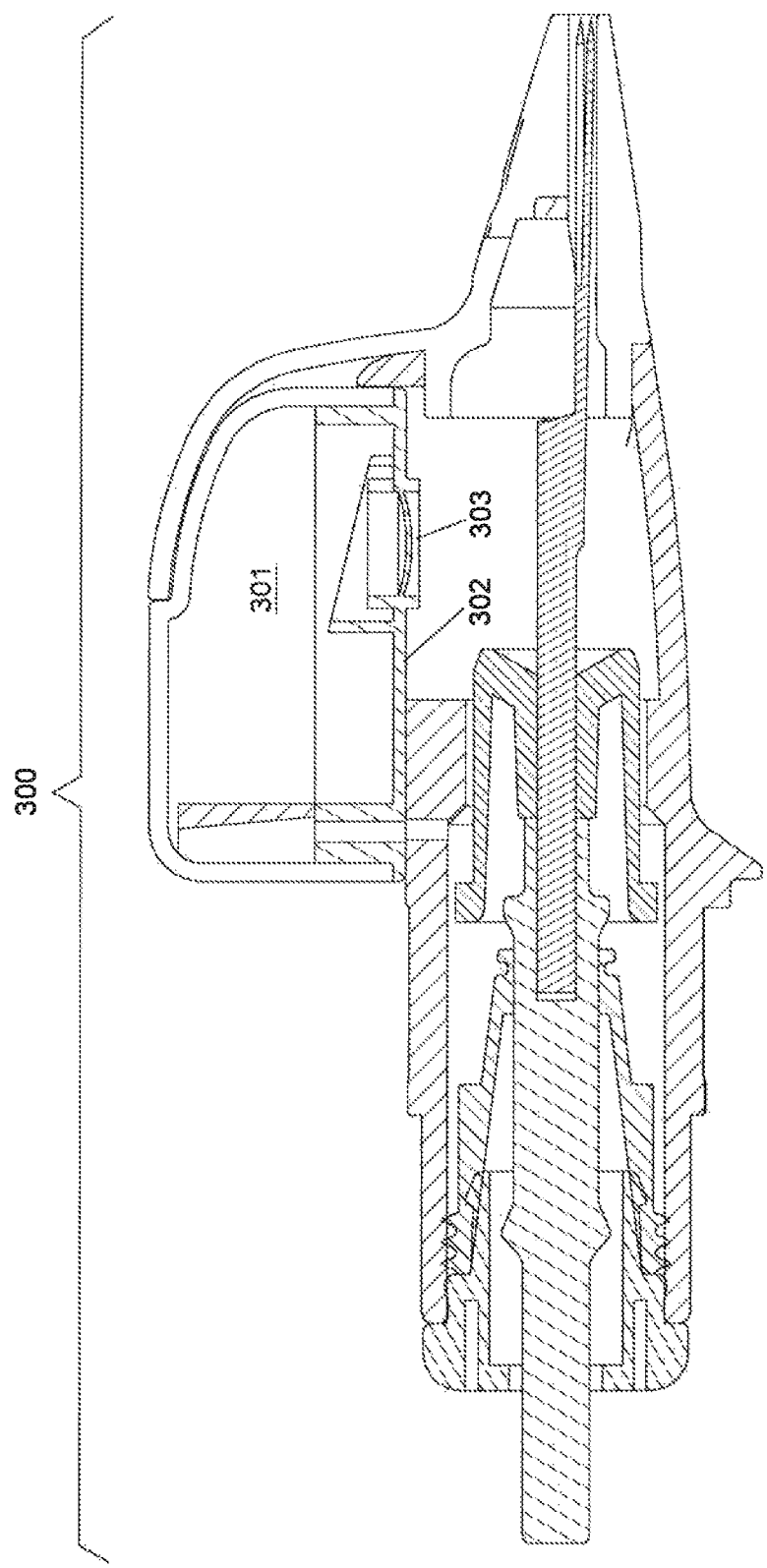

ated into the grip of a new custom-made tattooing device.
INK SUPPLY UNIT FOR A TATTOOING DEVICE

BACKGROUND OF THE INVENTION

1. The Field of the Invention

The present invention relates to an ink supply unit for supplying the needles of a tattooing device.

2. The Relevant Technology

Various types of tattooing devices are known, which generally comprise:
- a grip for gripping by a user;
- a removable tip provided at the end with one or more tattooing needles;
- drive means associated with the grip, for example an electric motor, for moving the needles of the device by imparting a reciprocating rectilinear motion to them.

In essence, such electric motor ensures the needles go under the skin without perforating the epidermis, and therefore with such a depth as to apply the desired tattoo without damaging the person's body.

The oscillating frequency of the needles generally is comprised between 60 and 160 Hz and may be varied according to the type of skin treated and the area of the body on which the tattoo is applied.

An important parameter in this regard is the depth of the needles because the tattoo artist decides how deep the tattooing device is to go to apply the tattoo in an effective and safe manner.

The ink usually is put into an external container from which it is taken by dipping the device into it, as though it were a fountain pen.

Alternatively, it is possible to also insert a pump into the device which sucks the ink from the container, or to use an external pump with which the ink is sucked from an external tank and is blown into the tip. At times, such pump is integrated in the device itself.

Then there are some types of more recent devices which also comprise an ink tank integrated therewith in a single body or insertable into the device themselves.

However, the tattooing devices of known type have certain drawbacks.

One drawback is represented by the fact that the devices of known type do not allow controlling the flow of ink dispensed when tattoos are applied.

A further drawback is represented by the fact that the tattooing devices of known type often require cleaning the needles when the colour of the ink used is to be changed, and this is an operation that requires keeping the electric motor in operation in order to clean the ink well. This need is due to the fact that the ink for applying tattoos is rather dense and therefore cleaning with the motor turned off would not be effective.

However, the fact that the electric motor remains operational during the cleaning of the needles results in the fact that a given quantity of ink in the tank is dispensed also during the cleaning of the needles and that therefore compromises the cleaning of the needles themselves.

Document GB 1331024 A describes a device for marking animals by means of ink introduced in a filling hole.

Document KR 101 831 124 B1 describes a tattooing device that comprises ink dispensing means and means for the exit/return of the needles, arranged in series in a housing that can be handled by a user.

Document WO 2015/127909 A1 describes a device configured in the manner of a cartridge, for introducing substances into the human skin.

Document ES 1069167 describes machinery for applying tattoos comprising a piston housed in a dispenser containing ink.

SUMMARY OF THE INVENTION

The present invention intends eliminating the aforesaid drawbacks.

In particular, it is the object of the present invention to make a tattooing device that is capable of dispensing the ink in such a manner as to control the dispensing flow of the ink during the application of the tattoo itself, and therefore in a more accurate manner.

It is a further object of the present invention to make a tattooing device capable of interrupting the outlet of ink during the cleaning of the needles, thus obtaining efficient cleaning.

The aforesaid objects are achieved by an ink supply unit for supplying the needles of a tattooing device according to the main claim.

Further detailed features of the invention are the object of the dependent claims.

Advantageously, the ink supply unit according to the invention allows controlling the ink flow by taking advantage of the reciprocating rectilinear movement of the needles of the tattooing device with which it is associated.

Again advantageously, the ink supply unit according to the invention, according to a preferred implementation embodiment, is also provided with a shaped cover element configured to prevent the outlet of the ink during the cleaning of the needles of the tattooing device with which it is associated.

Again advantageously, the ink supply unit according to the invention can be associated with the tip of the tattooing device with which it is associated or it can be integrated in the grip of a new custom-made tattooing device.

BRIEF DESCRIPTION OF THE DRAWINGS

The aforesaid objects and the aforesaid advantages will be better noted during the description of a preferred implementation embodiment of the invention, which is given below by way of a non-limiting indicative example, with reference to the accompanying drawings, in which:

FIG. 3 depicts a longitudinal sectional view of the ink supply unit of FIG. 1;

FIG. 5 depicts a sectional view of a detail of FIG. 3 taken along the section line V-V;

FIG. 5a depicts an enlarged view of a detail of FIG. 5;

FIG. 12 depicts a sectional view of a variant of a tattooing device comprising an implementation variant of the ink supply unit of FIG. 2 that can be applied to the devices already being used.

DETAILED DESCRIPTION OF THE PREFERRED EMBODIMENTS

Figure 1B:
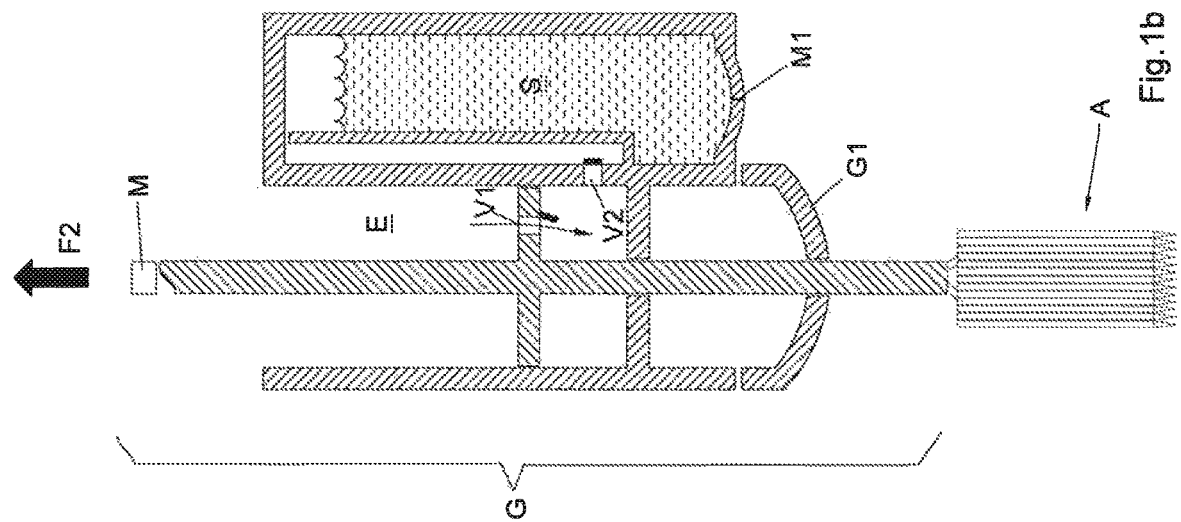
FIGS. 1a and 1b depict two schematic views showing two different operating steps of the ink supply unit of the invention.
Figure 1A:
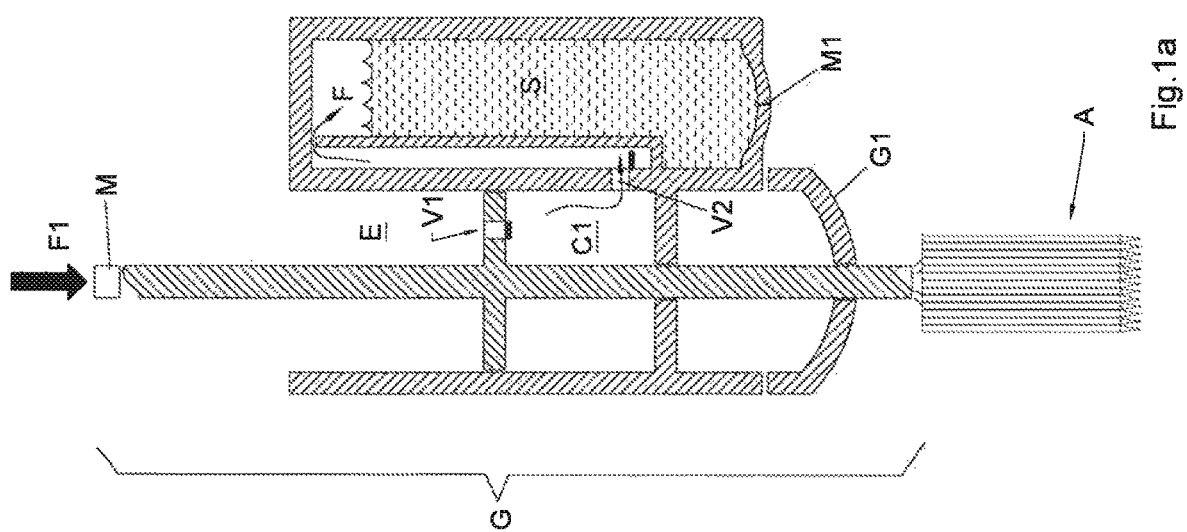

With reference to the diagram in FIGS. 1a and 1b, it depicts an ink supply unit, indicated as a whole with G, which conveys ink toward the needles A of a tattooing device and is connected thereto by means of a ring nut G1.

The needles A of the tattooing device are put into movement by drive means M configured so as to give the needles A a reciprocating rectilinear motion.

When the needles A moved by the drive means M move according to the direction of the arrow F2 (see FIG. 1b), a first valve V1 opens that lets air from the external environment E into a chamber C1.

There is also a second valve V2 laterally to the chamber C1, which valve remains closed when the valve V1 remains open.

When the needles A instead are moved according to the direction of arrow F1 (see FIG. 1a), the air in the chamber C1 is conveyed into a tank S by means of the second valve V2.

In this step, the first valve V1 remains closed.

The air is introduced into the tank S according to the direction of the arrow F and pushes the ink therein until it comes out of it by means of a membrane M1 and falls by gravity onto the needles A.

In this step, the air introduced into the tank S replaces the volume previously occupied by the ink pushed out of the tank S itself.

Then the cycle is repeated with the needles A moved according to the direction of the arrow F2 and the air introduced into the chamber C1 (see FIG. 1b) again.

This is the schematic explanation of the operation of the ink supply unit G according to the present invention and with reference to the diagram in FIGS. 1a and 1b.

Now, a first implementation embodiment of the ink supply unit G according to the invention is described below, referring to FIGS. 2 to 11.

Figure 2:
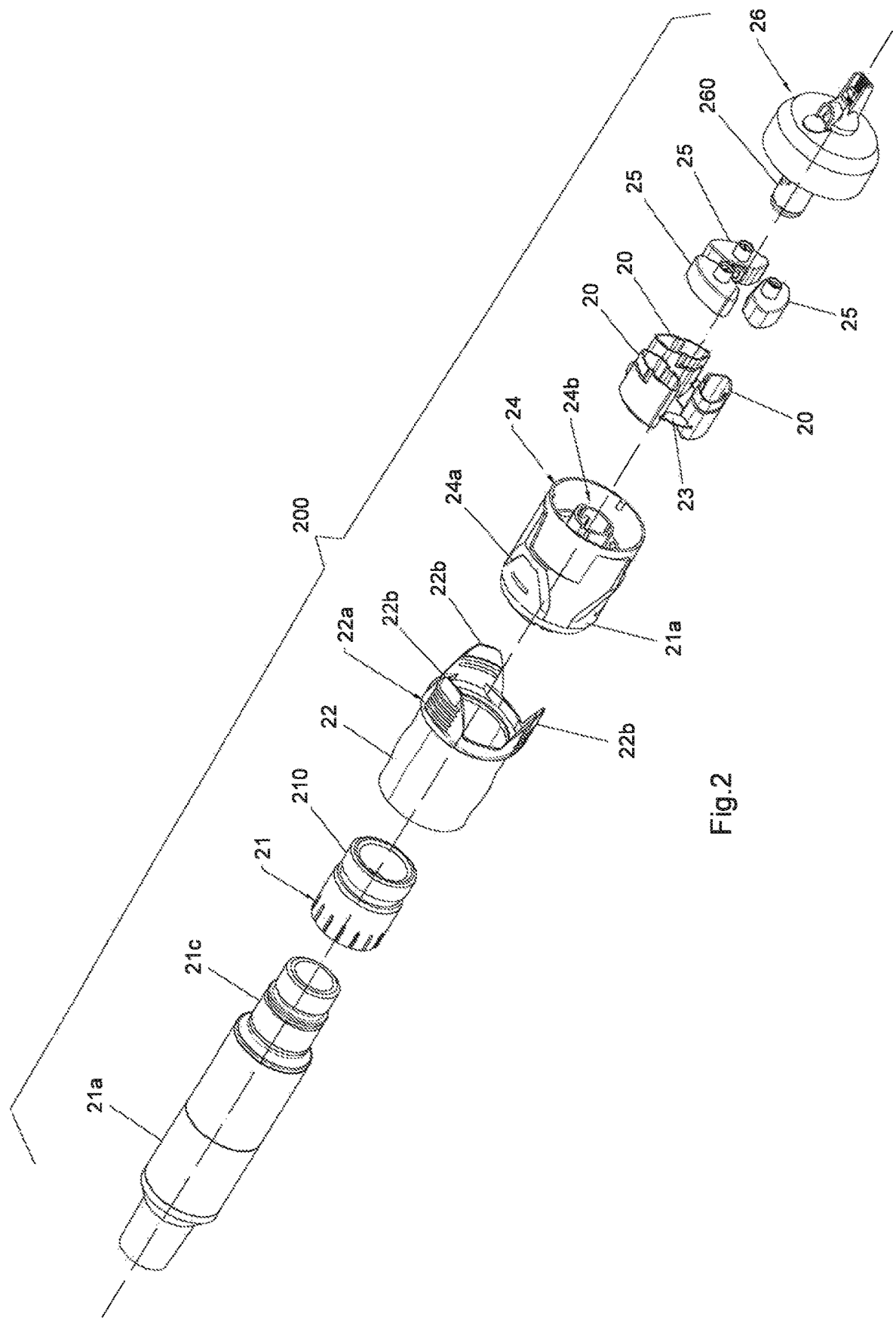
FIG. 2 depicts an exploded axonometric view of a tattooing device comprising an ink supply unit according to the invention.

FIG. 2 depicts a tattooing device 200 comprising:
a grip 21a;
a coupling element, depicted in this case by a ring nut 22a;
a fixed adapter 21 adapted to be coupled to the grip 21a;
a protective element 22 depicted by a cellophane guard configured to prevent the tattoo artist from getting dirty/infected with the blood of the person being tattooed;
three tanks 20 connected to one another by means of connecting elements 23;
an ergonomic grip element 24 arranged between the ring nut 22a and the tanks 20;
three lids 25 for closing each of the tanks 20;
a cover element 26 adapted to prevent the ink from accidentally coming out, as is better illustrated below.

The ergonomic grip element 24, the tanks 20, the lids 25 and the cover element 26 are components that, once assembled, give life to a tip 21b into which needles 5 are then inserted (shown in FIG. 3).

With reference to the exploded view of FIG. 2, the tattooing device 200 is assembled as follows.

The fixed adapter 21 is screwed onto the upper part 21c of the fixed grip 21a; then the ring nut 22a is coupled by coupling its fins 22b with the surfaces 24a of the grip element 24.

Then the upper end 210 of the fixed adapter 21 is coupled to the inner walls 240 (shown in FIG. 3) of the grip element 24.

Then the tanks 20 are inserted into the grip element 24, each of them already previously closed by one of the lids 25.

The cover element 26 is then coupled to the grip element 24 by inserting its protrusion 260 into the hole 24b of the grip element 24.

Advantageously, the ring nut 22a serves a dual function:
allowing the adjustment in depth of the length of the needles 5 (shown in FIG. 3) according to the area of the body to be tattooed and to how deep it is wanted to go into the skin of the person to be tattooed;
allowing the protective element 22 to be blocked in order to prevent the tattoo artist from getting dirty and therefore getting infected with the blood of other people.

With regard to the number of tanks 20, there are three in the present implementation embodiment, but it is apparent that there may be a different number.

The number of tanks may vary according to, for example, the number of colours to be used during the application of the tattoo.

In the example at hand, three different colours may be introduced, one for each tank 20, thus avoiding the need to fill an external container each time with an ink of a different colour.

FIG. 3, which depicts the assembly of the previously-described components of FIG. 2, illustrates the ink supply unit for the needles 5 of the tattooing device 200. The ink supply unit G is of the type comprising a handling unit 2 in which the following can be found:
a grip 21a;
a tip 21b consisting of a complex removable assembly provided at the end of a plurality of needles 5 for applying tattoos;
a ring nut 22a for connecting the grip 21a and the tip 21b to each other;
drive means 7 (schematically depicted in FIG. 3) configured to move the needles 5, by imparting a reciprocating rectilinear motion to them.

Preferably but not necessarily, the drive means 7 consist of an electric motor provided with an eccentric that drives a rod 8 associated therewith, with which a needle-holder support device 9 is associated, which in turn is connected to a needle-holder 10 that supports the needles 5.

Figure 4:
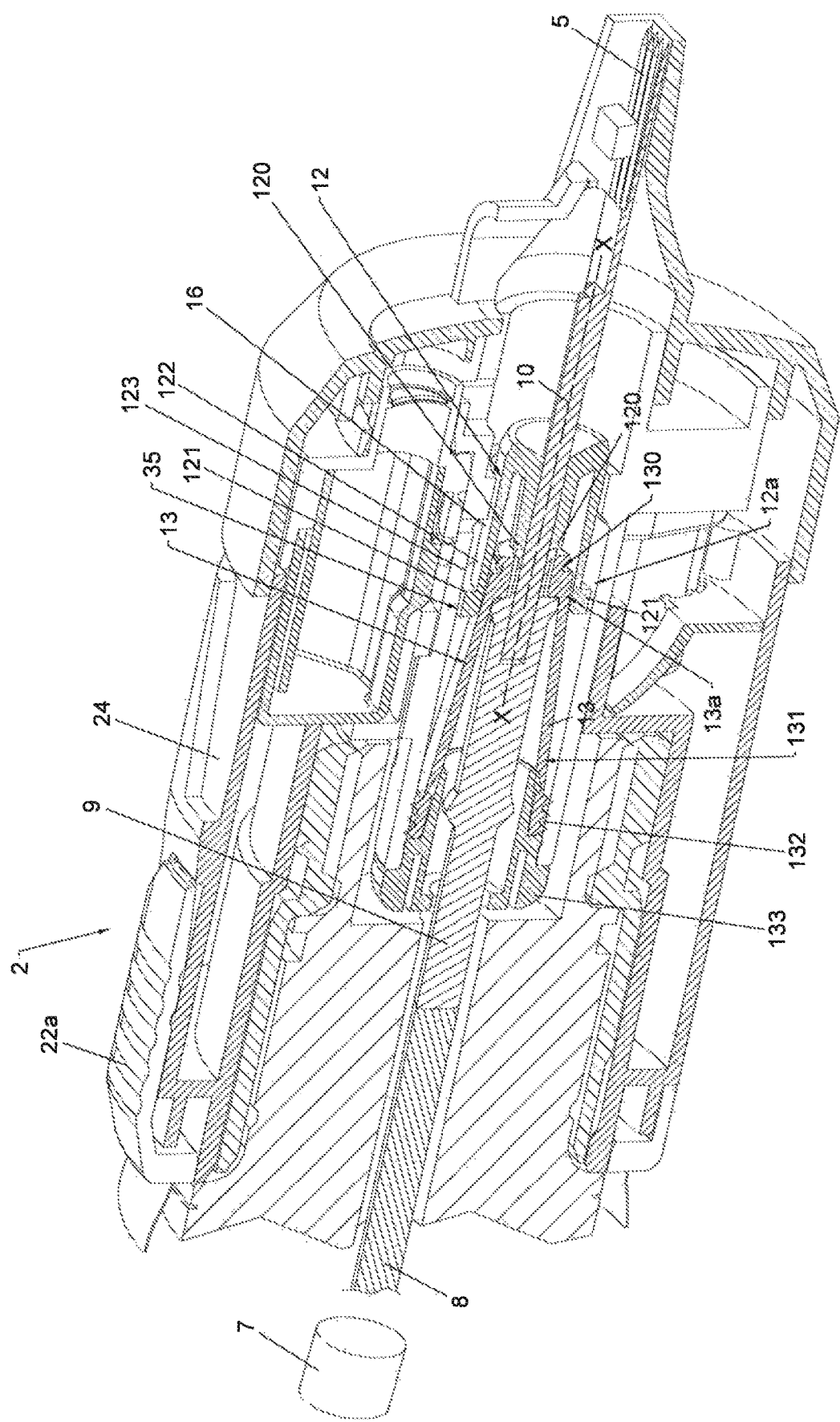
FIG. 4 depicts a different longitudinal sectional view of the ink supply unit of FIG. 1.

As shown in FIGS. 3 and 4, an air movement unit 11 is associated with the handling unit 2, which air movement unit comprises:
a piston 12 on which the needle-holder 10 is fitted; the piston 12 has an annular cross section in which there are found two shaped appendages 120 and two shaped protrusions 121 configured to be stably coupled on the needle-holder 10;
an elastic casing 13 coupled to the piston 12 and coaxial thereto according to a symmetry axis X coinciding with the symmetry axis of the needle-holder 10.

As shown in FIG. 4, the elastic casing 13 has a substantially annular first stretch 130 fitted on the needle-holder 10 and a second elongated stretch 131, joined to the first stretch 130, having a shaped end 132 that rests on an underlying abutment element 133.

The lower part 12a of the piston 12 is coupled with the upper part 13a of the elastic casing 13 so that the elastic casing 13 can transmit the movement to the piston 12 in order to then move the needles 5, as is described in greater detail below.

According to an implementation variant no depicted in the drawings, another elastic means can be used in place of the elastic casing 13.

The expression "elastic means" here means any element capable of bringing the needles 5 back into their resting position, such as for example, a spring, an elastic ring or also a transducer or a magnet.

With reference to FIG. 4, an annular chamber 16 is defined between the wall 122 of the shaped appendage 120 of the piston 12 and a delimiting wall 123.

Advantageously, the propagation of the air toward the annular chamber 16 is allowed by means of a series of couplings with clearance between the inner mechanical parts of the tattooing device 200, as better described below.

Thus, the elasticity of the casing 13 allows the rod 8 to return to resting position at each axial oscillation, and with it also the needle-holder device 10 and the needles 5, as better illustrated below.

The term "axial oscillation" in this description is meant as a synonym of "reciprocating rectilinear motion".

As shown in FIG. 5, the air pushed into the annular chamber 16 is directed in unambiguous direction, following the direction of the arrow F4 (shown in FIG. 5a), into an adjacent tank 20 containing ink first passing through a convenient series of orifices, respectively 17, 18, 19, of which orifice 18 performs the function of the valve V2 in FIG. 1. The path of the air crossing such orifices is depicted more clearly in the detail of FIG. 5a.

Advantageously, always with reference to FIG. 5a, the orifice 19 communicates with a channel 19a the geometry of which defines a labyrinthine path such as to avoid ink jets that are too fast and therefore are not manageable.

Figure 7:
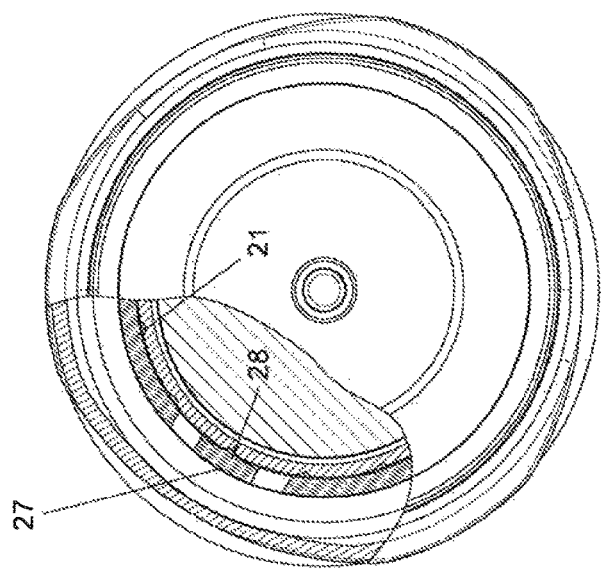
FIG. 7 depicts a partial section of FIG. 6 along the section line VII-VII.
Figure 8:
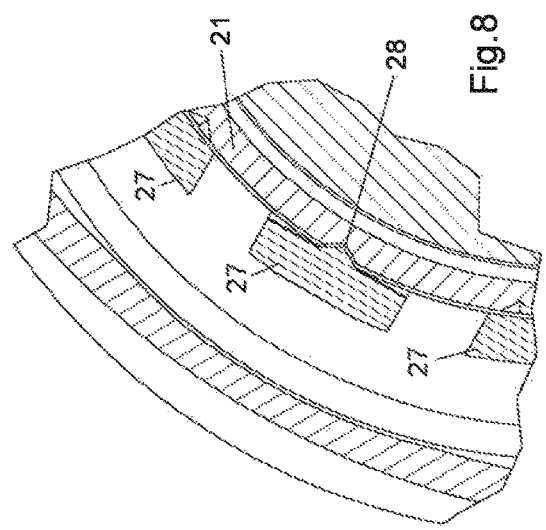
FIG. 8 depicts an enlargement of FIG. 7.
Figure 6:
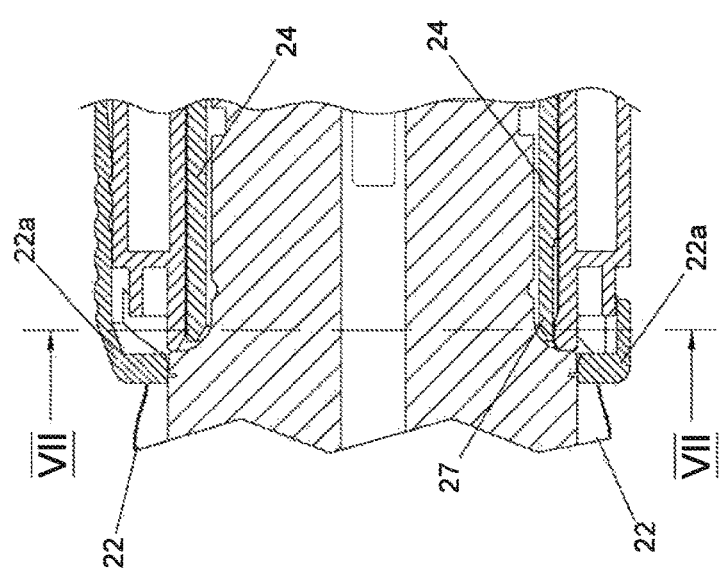
FIG. 6 depicts a sectional view of another detail of FIG. 3.

The adjustment of the length of the needles 5 is illustrated in the details of FIGS. 6 to 8.

As shown in FIG. 6, the ergonomic grip element 24 has a plurality of teeth 27, shown in FIGS. 7 and 8, having a V-shaped cross section and a profile matched with the one of a corresponding shaped recess 28 made in the fixed adapter 21.

The above-illustrated configuration of the teeth 27 is non-limiting; indeed, implementation variants not herein depicted in which the teeth 27 may have a different profile, are possible.

Advantageously, by rotating the ring nut 22a, a reasonable adjustment is allowed of the ergonomic grip element 24 to adjust the length of the needles 5, and therefore also the protrusion thereof, and therefore the depth is adjusted with which the ink is injected below the skin of the person to be tattooed. In essence, it is a very accurate mechanical trigger adjustment that allows a reasonable adjustment of the length of the needles 5.

Figure 9:
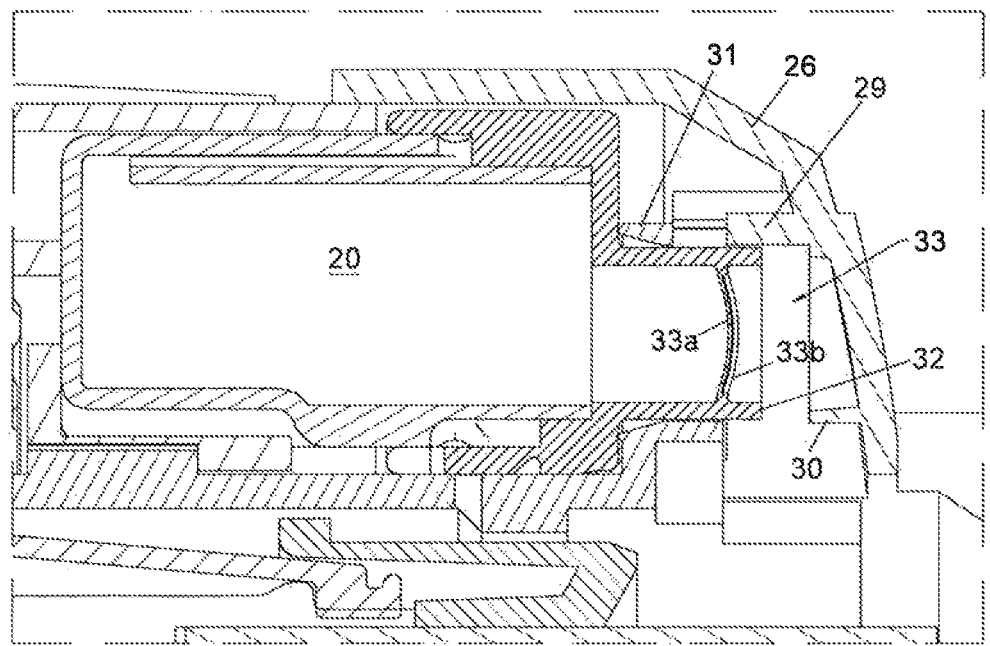
FIGS. 9 and 10 depict respectively two sections of two different operating configurations of a detail of FIG. 2.
Figure 10:
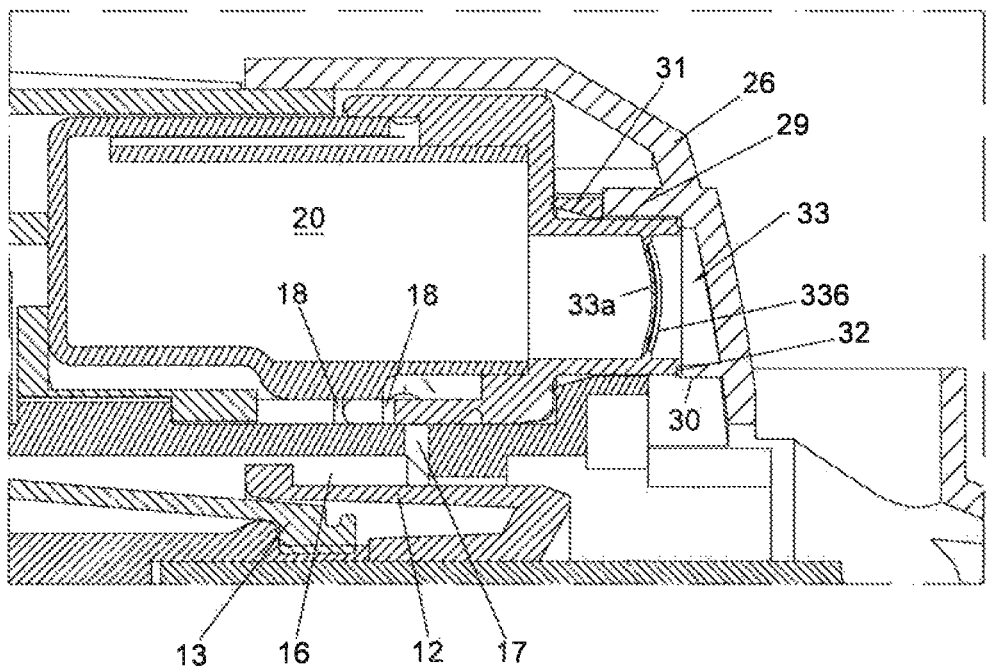

With reference to FIGS. 9 and 10, the tank 20 has a membrane 33a at one end belonging to an outlet mouth 33, through which the ink, pushed by the air introduced into the tank 20, comes out and falls by gravity back onto the needles 5 that apply the tattoo.

The path of the ink that comes out is indicated by the arrow F3 in FIG. 3.

In the present implementation embodiment, the membrane 33a is a rubber membrane having a slit 33b (shown in FIGS. 9 and 10) that opens when a given pressure threshold value is exceeded, thus allowing a regular and continuous flow of ink.

FIGS. 9 and 10 illustrate a sectional view of a further feature of the tattooing device 200.

Generally, when the tattoo artist is to wash the needles 5 of the ink, he/she also operates the drive means 7, but such operation could also involve a given quantity of ink coming out during the cleaning thereof.

To obviate such drawback, a cover element 26 is depicted in a sectional view in FIGS. 9 and 10, which takes on two configurations, and precisely:
  a first configuration in which the cover element 26 is uncoupled from the tank 20 and thus allows the ink to come out, as shown in FIG. 9;
  a second configuration in which the cover element 26 translates axially so that the shaped protrusions 29 and 30 abut respectively on a stop element 31 associated with the tank 20, and on an end 32 of the outlet mouth 33, thus preventing the ink from coming out during the cleaning operation of the needles 5, as shown in FIG. 10.

According to an implementation variant not depicted in the drawings, rather than translating, the cover element 26 may move by roto-translation movement.

Figure 11:
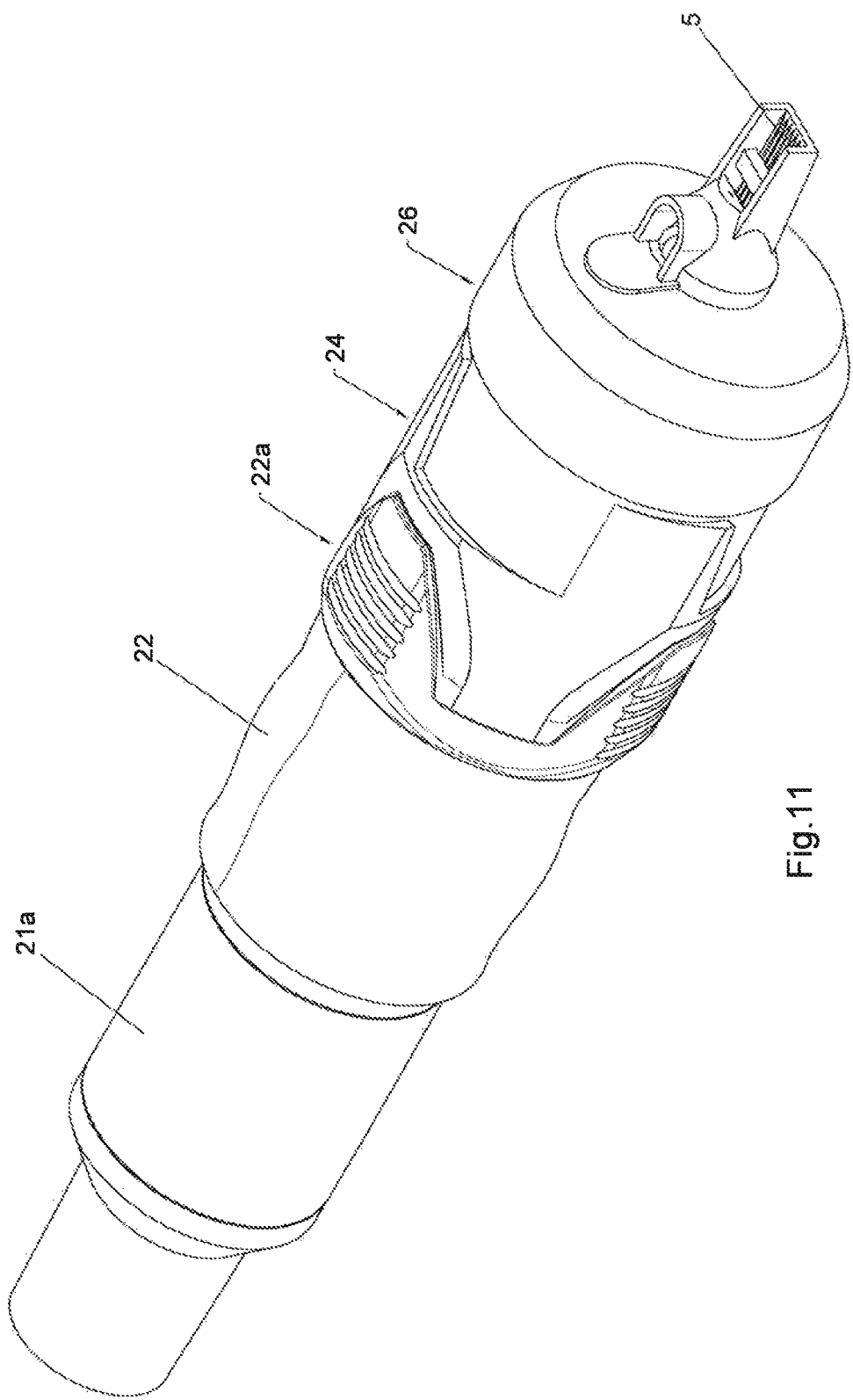
FIG. 11 depicts an axonometric view of the assembled ink supply unit of FIG. 2.

The tattooing device 200 is depicted in FIG. 11 in the assembled configuration thereof, in which the grip 21a, the protective element 22, the ring nut 22a, the ergonomic grip element 24, the cover element 26 are clearly shown.

Operatively and with reference to FIGS. 2 to 11, the ink supply unit G according to the invention operates as follows.

The tattoo artist first fills the tanks 20 with the desired ink colours, or buys them already filled and sealed, and then closes the device 200 and begins applying the tattoo.

The tattoo artist then operates the electric motor 7 that moves the rod 8 and starts up the needle-holder support 9 and therefore the needle-holder 10 with the needles 5 therein, which move with reciprocating rectilinear motion to dispense the ink.

Indeed, by moving the piston 12 and the elastic casing 13, the electric motor 7 allows dispensing the air that comes in from the outside, through convenient openings, up to being conveyed toward the annular chamber 16 through a gap 35.

The air is pushed by the piston 12 (FIG. 5a) in the annular chamber 16 and exits through the orifices 17, 18, 19, shown in FIGS. 5 and 5a, and finally is conveyed through the channel 19a toward the tank 20. It is worth noting that the passage of the air generated by the drive means 7 in the annular chamber 16 is facilitated by the fact that the couplings between the mechanical members are not sealing couplings but rather couplings with a clearance. Here, it is the presence of a coupling with a clearance between the various mechanical members to allow the operation of the whole system.

The air pushed into the tank 20 creates an overpressure that pushes the ink therein outward, and in particular onto the needles 5.

In the meantime, the drive means 7 push the rod 8, which moves the elastic casing 13, which in turn moves the piston 12, the needle-holder support 9 and the needle-holder 10 with the needles 5. These mechanical members all move integrally and are coaxial to one another according to the longitudinal axis X of the needle-holder 10.

Once the tattooing operation is complete, the electric motor 7 is turned off and the needles 5 are caused to return into the device 200 by means of the elastic casing 13 which also brings the piston 12, the needle-holder support 9 and the needle-holder 10 back to resting position.

This happens in light of the fact that the piston 12, the elastic casing 13, the needle-holder support 9 and the needle-holder 10 are integral with one another.

When the tattoo artist intends cleaning the needles 5, in the case of the device 200, he/she closes the latter by means of the cover element 26, thus preventing the ink to come out during the cleaning operation.

FIG. 12 depicts the sectional view of an implementation variant of a tattooing device, depicted now as a whole with 300, which differs from the previous implementation embodiment for the fact that the tank 301 now has a different shape and is provided with a cover 302 having a safety tongue which once removed, reveals a membrane valve 303.

Substantially, the membrane valve 303 replaces the membrane 33a with the relative slit 33b (see FIGS. 9 and 10) of the above-described implementation embodiment acting as valve for preventing the ink from coming out.

This implementation variant may be assembled on the currently most used tattooing devices, in place of the standard tips.

Otherwise, the operation of the implementation variant of the device 300 is similar to the one of the first implementation embodiment described relative to the device 200.

So far, two implementation embodiments have been illustrated in which the air movement unit and the tank of the tattooing device were associated with the tip of the device itself.

However according to an implementation variant not depicted, it is also possible for the air movement unit and the tank to be associated with the grip of the device rather than with the tip, thus giving rise to a further implementation embodiment in which the ink supply unit G of the invention is integrated in the tattooing device.

As is apparent from what is described, the ink supply unit according to the invention achieves the pre-set objects.

The object was achieved of making a tattooing device that is capable of dispensing the ink in a more accurate manner with respect to the known art because the ink dispensing flow when the tattoo is being applied is proportional to the oscillation frequency of the needles.

This has now become possible by means of an air movement unit in turn started up by an electric motor or by an equivalent system that imparts the reciprocating rectilinear motion to the needles.

Moreover, the exiting ink flow is regulated by means of a membrane having a slit that only opens after a given pressure threshold value is exceeded.

The object was also achieved of making a tattooing device capable of avoiding the ink from coming out during the cleaning of the needles. This was possible by means of a specific cover element or by means of a convenient membrane of the tank containing the ink.

In the case the ink tanks are integrated with the tattooing device grip in the selling step, they may be sold sealed and pre-filled and, in the case the user is to change colour, a roto-translation movement is sufficient to change the colour cartridge.

If instead the ink tank is to be hooked to the tip of the device, then the individual colour tank may be provided with an integrated ring that can be axially hooked to the needle-holder; alternatively, the individual tank may be radially hooked to the needle-holder.

Modifications and/or variants may be made to the ink supply unit according to the invention in implementation step, which although they have not been described, are to be intended as protected by this patent should they fall within the scope of the following claims.

The invention claimed is:

1. A unit for supplying ink to the needles of a tattooing device, said device comprising a handling unit which comprises:
   a grip;
   a removable tip provided at one end with one or more tattooing needles;
   a coupling element configured to connect said grip and said tip to each other;
   drive means operatively associated with said grip to move said needles, by imparting a reciprocating rectilinear motion to them;
   an air movement unit driven by said drive means and mechanically connected to said handling unit;
   at least one tank for containing the ink, operatively associated with said handling unit,
   wherein said air movement unit is configured to push the air moved by said drive means towards said at least one tank, said at least one tank for containing the ink communicating with said air movement unit by means of valve means, in which, once conveyed into said at least one tank by means of said valve means, the air forces the ink to be dispensed from said at least one tank onto said needles.

2. The ink supply unit according to claim 1, wherein said air movement unit comprises:
   a piston on which a needle-holder is fitted which defines an annular chamber into which the air moved by said drive unit is pushed;
   an elastic means adapted to cause said needles to return to resting position, the lower part of said piston being coupled with the upper part of said elastic means.

3. The ink supply unit according to claim 2, wherein said cover element is configured to translate axially or to roto-translate, taking on:
   a first position wherein said shaped cover element is uncoupled from said tank, allowing the ink to come out;
   a second position wherein said shaped cover element is coupled to said tank by means of first and second abutment members, preventing the ink from coming out of the tank itself.

4. The ink supply unit according to claim 3, wherein said first abutment members consist of two shaped protrusions belonging to said cover element, and in that said second abutment members consist of a stop element associated with said at least one tank and with an end of the outlet mouth of said at least one tank.

5. The ink supply unit according to claim 1, wherein said tip comprises:
   said at least one tank for containing the ink;
   an ergonomic grip element interposed between said coupling element and said at least one tank;
   a cover element adapted to be inserted into said ergonomic grip element and to contain said needles.

6. The ink supply unit according to claim 1, further comprising a length adjustment device of the needles of said tip.

7. The ink supply unit according to claim 6, wherein said length adjustment device of said needles comprises:
   a shaped tooth belonging to a substantially tubular grip member adapted to be coupled to said grip;
   a shaped recess having a profile which can be matched with the profile of said shaped tooth, said shaped tooth and said shaped recess acting in conjunction with each other to allow adjusting the length of said needles in reasonable manner.

8. The ink supply unit according to claim 6, wherein said tip and said air movement unit are coaxial with respect to a longitudinal axis of said needle-holder and are integral with each other.

9. The ink supply unit according to claim 1, further comprising a channel for supplying the air that exits said annular chamber towards the tank itself according to a labyrinthine path.

10. The ink supply unit according to claim 1, wherein said at least one tank for containing the ink and said air movement unit are associated with said grip.

11. The ink supply unit according to claim 1, wherein said at least one tank for containing the ink and said air movement unit are associated with said tip.

* * * * *